US011561359B2

(12) United States Patent
Liu et al.

(10) Patent No.: US 11,561,359 B2
(45) Date of Patent: Jan. 24, 2023

(54) BALANCING DEVICE FOR ROTARY APPARATUS

(71) Applicant: Carl Zeiss Meditec AG, Jena (DE)

(72) Inventors: Chencai Liu, Shanghai (CN); Jianwei Shu, Hangzhou (CN)

(73) Assignee: Carl Zeiss Meditec AG, Jena (DE)

( * ) Notice: Subject to any disclaimer, the term of this patent is extended or adjusted under 35 U.S.C. 154(b) by 161 days.

(21) Appl. No.: 16/262,961

(22) Filed: Jan. 31, 2019

(65) Prior Publication Data

US 2019/0250360 A1    Aug. 15, 2019

(30) Foreign Application Priority Data

Feb. 9, 2018  (CN) .......................... 201810132134.7
Feb. 9, 2018  (CN) .......................... 201820230284.7

(51) Int. Cl.
G02B 7/00 (2021.01)
A61B 90/25 (2016.01)
A61B 90/50 (2016.01)
F16M 11/06 (2006.01)

(52) U.S. Cl.
CPC .............. *G02B 7/001* (2013.01); *A61B 90/25* (2016.02); *A61B 90/50* (2016.02); *F16M 11/06* (2013.01); *A61B 2090/5025* (2016.02); *F16M 2200/044* (2013.01)

(58) Field of Classification Search
CPC .... G02B 7/001; H02K 7/1166; H02K 49/046; H02K 7/12; H02K 7/04; H02K 49/106; H02K 49/108; H02K 16/00; H02K 29/06; H02K 49/043; H02K 11/215; A61B 90/50; A61B 90/25; A61B 2090/5025; A61B 34/30; A61B 2090/508; A61B 90/20; A61B 1/00149; A61B 2090/064; A61B 2090/066; F16M 11/06; F16M 2200/044; B62K 11/007; B25J 19/0004; B25J 19/0008; G01M 1/30
See application file for complete search history.

(56) References Cited

U.S. PATENT DOCUMENTS 2,771,171 A * 11/1956 Schultz ..................... F16D 7/02
                                                                    192/84.3
2,807,734 A *  9/1957 Lehde ..................... H02K 49/02
                                                                    310/103

(Continued)

FOREIGN PATENT DOCUMENTS

WO    WO-2017015764 A1 *  2/2017 .......... B25J 19/0008

*Primary Examiner* — Jonathan Liu
*Assistant Examiner* — Taylor Morris
(74) *Attorney, Agent, or Firm* — Ewers IP Law PLLC; Falk Ewers (57) ABSTRACT

A balancing device for a rotary apparatus including a rotary body which is configured to pivot or swivel about at least one rotary shaft is provided. The balancing device includes a magnet assembly and a torque adjusting mechanism. The magnet assembly includes a combination of two or more magnets, and the torque adjusting mechanism is configured to adjust a torque generated by the combination of the two or more magnets. The balancing device generates an output torque in the form of a cosine curve or sine curve which optimally matches with an unbalancing torque of the rotary body. The balancing device has a small size and is invulnerable to fatigue failure.

22 Claims, 6 Drawing Sheets

(56) References Cited

U.S. PATENT DOCUMENTS

| | | | | |
|---|---|---|---|---|
| 3,050,646 A * | 8/1962 | Eddy | H02K 49/106 | 310/104 |
| 3,394,295 A * | 7/1968 | Cory | H02K 21/16 | 318/115 |
| 3,407,318 A * | 10/1968 | Korthaus | H02K 7/1125 | 310/75 R |
| 3,555,321 A * | 1/1971 | Gruener | B41J 19/02 | 310/99 |
| 3,822,390 A * | 7/1974 | Janson | B65H 59/04 | 310/104 |
| 3,934,216 A * | 1/1976 | Ward | H01F 7/0242 | 335/272 |
| 4,115,040 A * | 9/1978 | Knorr | H02K 49/106 | 310/104 |
| 4,152,617 A * | 5/1979 | Janson | H02K 49/00 | 310/103 |
| 4,163,164 A * | 7/1979 | Pieters | F04D 13/027 | 310/103 |
| 4,239,092 A * | 12/1980 | Janson | F16D 27/01 | 188/267 |
| 4,371,798 A * | 2/1983 | Kuroda | H02K 49/10 | 310/103 |
| 4,381,466 A * | 4/1983 | Laenens | H02K 49/106 | 310/103 |
| 4,943,019 A * | 7/1990 | Mester | B66F 11/048 | 248/123.11 |
| 5,064,029 A * | 11/1991 | Araki | H02K 49/043 | 188/267 |
| 5,096,024 A * | 3/1992 | Wu | H02K 49/043 | 188/164 |
| 5,158,279 A * | 10/1992 | Laffey | B65H 3/5261 | 192/11 OR |
| 5,204,572 A * | 4/1993 | Ferreira | H02K 49/106 | 310/156.19 |
| 5,248,940 A * | 9/1993 | Patience | F04D 13/024 | 324/207.15 |
| 5,254,061 A * | 10/1993 | Leask | A63B 21/0052 | 482/5 |
| 5,288,043 A * | 2/1994 | Tigliev | A61B 90/25 | 248/123.11 |
| 5,437,353 A * | 8/1995 | Wu | A63B 21/0051 | 188/164 |
| 5,455,473 A * | 10/1995 | Lipo | H02K 19/24 | 310/115 |
| 5,468,201 A * | 11/1995 | Minoura | A63B 69/16 | 482/61 |
| 5,480,114 A * | 1/1996 | Nakamura | F16M 11/126 | 248/123.2 |
| 5,492,296 A | 2/1996 | Biber | | |
| 5,528,417 A * | 6/1996 | Nakamura | A61B 50/28 | 359/384 |
| 5,583,408 A * | 12/1996 | Lowrance | B25J 21/005 | 318/568.1 |
| 5,675,203 A * | 10/1997 | Schulze | B60L 15/2054 | 310/113 |
| 5,779,456 A * | 7/1998 | Bowes | F04D 13/027 | 417/420 |
| 5,783,885 A * | 7/1998 | Post | F16C 39/063 | 310/103 |
| 5,793,826 A * | 8/1998 | Sato | H02K 49/106 | 376/245 |
| 5,831,364 A * | 11/1998 | Buse | F04D 13/027 | 310/156.19 |
| 5,880,548 A * | 3/1999 | Lamb | H02K 49/046 | 310/78 |
| 6,041,571 A * | 3/2000 | Fields | B65B 7/2835 | 53/331.5 |
| 6,099,467 A * | 8/2000 | Kehr | A61B 1/00188 | 359/822 |
| 6,129,194 A * | 10/2000 | Booth | F16D 27/112 | 192/84.941 |
| 6,186,023 B1 * | 2/2001 | Nakamura | F16M 11/126 | 74/490.01 |
| 6,218,751 B1 * | 4/2001 | Bohlin | F16C 32/0417 | 310/90.5 |
| 6,234,938 B1 * | 5/2001 | Chen | A63B 21/00192 | 188/161 |
| 6,429,611 B1 * | 8/2002 | Li | H02K 21/14 | 318/115 |
| 6,555,941 B1 * | 4/2003 | Zepp | H02K 21/024 | 310/114 |
| 6,682,430 B2 * | 1/2004 | Killen | H02K 49/046 | 192/84.5 |
| 6,737,778 B2 * | 5/2004 | Daikoku | H02K 7/1008 | 310/112 |
| 6,841,909 B2 * | 1/2005 | Six | H02P 15/02 | 310/103 |
| 6,943,478 B2 * | 9/2005 | Zepp | H02K 21/222 | 310/191 |
| 7,034,427 B2 * | 4/2006 | Hirzel | H02K 7/12 | 310/156.35 |
| 7,219,864 B2 * | 5/2007 | Strauss | A61B 90/25 | 248/122.1 |
| 7,294,947 B2 * | 11/2007 | Corbin, III | H02K 49/02 | 310/103 |
| 7,598,646 B2 * | 10/2009 | Cleveland | B62J 6/06 | 310/156.43 |
| 7,741,746 B2 * | 6/2010 | Groening | H02K 49/106 | 310/106 |
| 7,863,789 B2 * | 1/2011 | Zepp | H02K 21/024 | 310/90 |
| 7,960,888 B2 * | 6/2011 | Ai | H02K 7/12 | 310/190 |
| 8,221,247 B2 * | 7/2012 | Lai | H02K 49/106 | 464/29 |
| 8,240,447 B2 * | 8/2012 | Ueda | F16D 27/01 | 192/84.3 |
| 8,904,900 B2 * | 12/2014 | Dorigatti | B25J 17/00 | 74/490.01 |
| 8,910,537 B2 * | 12/2014 | Nakamura | A61B 90/50 | 901/21 |
| 9,103,150 B1 * | 8/2015 | Wong | F16M 11/2064 | |
| 9,638,273 B2 * | 5/2017 | Schmidt | F16D 49/00 | |
| 9,748,886 B1 * | 8/2017 | McDonald | B63H 21/14 | |
| 9,855,069 B2 * | 1/2018 | Jezierski | A61B 17/32002 | |
| 10,016,900 B1 * | 7/2018 | Meyer | A61B 34/30 | |
| 10,374,502 B2 * | 8/2019 | Diao | H02K 49/102 | |
| 10,589,935 B2 * | 3/2020 | Ragan | B65G 23/06 | |
| 2002/0093262 A1 * | 7/2002 | Zepp | H02K 21/024 | 310/90 |
| 2002/0186647 A1 * | 12/2002 | Her | H02K 49/108 | 369/266 |
| 2004/0066107 A1 * | 4/2004 | Gery | H02K 49/106 | 310/103 |
| 2004/0130228 A1 * | 7/2004 | Chang | F16D 27/01 | 310/103 |
| 2005/0104469 A1 * | 5/2005 | Zepp | H02K 11/21 | 310/191 |
| 2006/0261765 A1 * | 11/2006 | Prasanna | H02P 31/00 | 318/400.01 |
| 2007/0000741 A1 * | 1/2007 | Pribonic | H02K 49/046 | 188/267 |
| 2008/0054748 A1 * | 3/2008 | Huber | H02K 49/02 | 310/102 R |
| 2008/0105078 A1 * | 5/2008 | Gregor | F01L 1/352 | 74/568 R |
| 2008/0105503 A1 * | 5/2008 | Pribonic | H02K 49/046 | 188/267 |
| 2008/0150383 A1 * | 6/2008 | Groening | H02K 49/106 | 310/105 |
| 2009/0004037 A1 * | 1/2009 | Ito | F04C 29/0064 | 418/55.1 |
| 2009/0125024 A1 * | 5/2009 | Baur | A61B 18/14 | 606/42 |
| 2009/0163929 A1 * | 6/2009 | Yeung | A61B 34/30 | 606/130 |

(56) References Cited

U.S. PATENT DOCUMENTS

| | | | |
|---|---|---|---|
| 2010/0138127 A1* | 6/2010 | Boughtwood | B60L 15/2009 701/71 |
| 2010/0156227 A1* | 6/2010 | Hung | H02K 21/16 310/156.38 |
| 2010/0163694 A1* | 7/2010 | Fadler | A61B 8/4218 192/30 R |
| 2010/0308149 A1* | 12/2010 | Allington | A62B 1/08 242/379 |
| 2011/0037333 A1* | 2/2011 | Atallah | H02K 51/00 310/98 |
| 2011/0045932 A1* | 2/2011 | Fauteux | B25J 9/102 475/221 |
| 2011/0057530 A1* | 3/2011 | Chang | H02K 49/106 310/156.08 |
| 2011/0162476 A1* | 7/2011 | Nakamura | A61B 90/50 74/490.01 |
| 2012/0262017 A1* | 10/2012 | Mengibar Rivas | B67B 3/2086 310/103 |
| 2012/0296159 A1* | 11/2012 | Kanazawa | A61B 1/0014 600/102 |
| 2013/0123026 A1* | 5/2013 | Purdy | H02K 49/106 464/29 |
| 2013/0205558 A1* | 8/2013 | Sporer | A61B 90/50 29/407.01 |
| 2013/0285482 A1* | 10/2013 | Yamamoto | H02K 1/272 310/43 |
| 2013/0299299 A1* | 11/2013 | Hoffmann | F16D 27/004 192/84.9 |
| 2014/0157937 A1* | 6/2014 | Doi | F16M 11/2021 74/490.01 |
| 2014/0167545 A1* | 6/2014 | Bremner | H02K 49/10 310/103 |
| 2015/0042182 A1* | 2/2015 | Glover | H02K 16/00 310/46 |
| 2015/0171694 A1* | 6/2015 | Walsh | H02K 29/03 310/156.43 |
| 2015/0200582 A1* | 7/2015 | Headstrom | A61C 17/3445 310/25 |
| 2015/0250547 A1* | 9/2015 | Fukushima | B25J 9/1697 606/130 |
| 2015/0301553 A1* | 10/2015 | Rossa | F16D 67/06 477/7 |
| 2015/0369418 A1* | 12/2015 | Wong | F16M 11/041 248/372.1 |
| 2016/0036308 A1* | 2/2016 | Bailey | H02K 3/28 290/45 |
| 2016/0223031 A1* | 8/2016 | Atkinson | F16D 7/025 |
| 2016/0242728 A1* | 8/2016 | Niizeki | A61B 6/08 |
| 2016/0329795 A1* | 11/2016 | Ricci | H02K 1/2793 |
| 2016/0367334 A1* | 12/2016 | Devengenzo | A61B 34/30 |
| 2017/0027652 A1* | 2/2017 | Johnson | A61B 34/30 |
| 2017/0317573 A1* | 11/2017 | Mueller | H02K 49/102 |
| 2017/0353078 A1* | 12/2017 | Post | F16C 32/0436 |
| 2018/0014906 A1* | 1/2018 | Fukushima | A61B 90/50 |
| 2018/0110581 A1* | 4/2018 | Kamata | G02B 7/001 |
| 2018/0212500 A1* | 7/2018 | Bendixen | F04D 13/025 |
| 2018/0219452 A1* | 8/2018 | Boisclair | H02K 7/04 |
| 2018/0264655 A1* | 9/2018 | Kuroda | A61B 34/30 |
| 2018/0358870 A1* | 12/2018 | Kawanami | A61H 1/0266 |
| 2019/0046283 A1* | 2/2019 | Nagao | B25J 19/0004 |
| 2019/0109549 A1* | 4/2019 | Odagiri | H02K 7/1021 |
| 2019/0312497 A1* | 10/2019 | Walsh | H02K 11/21 |
| 2019/0328480 A1* | 10/2019 | Kamikawa | B25J 15/0019 |
| 2020/0129052 A1* | 4/2020 | Unai | A61B 1/00149 |
| 2020/0266682 A1* | 8/2020 | Goossens | H02K 7/125 |
| 2020/0343805 A1* | 10/2020 | Rhyu | H02K 49/106 |
| 2020/0386289 A1* | 12/2020 | Clymer | H02K 49/106 |

* cited by examiner

BALANCING DEVICE FOR ROTARY APPARATUS

CROSS REFERENCE TO RELATED APPLICATIONS

This application claims priority to Chinese patent applications CN 201820230284.7 and 201810132134.7, both filed on Feb. 9, 2018, and the entire contents of which are incorporated herein by reference.

TECHNICAL FIELD

The invention relates to a rotary apparatus having a rotary body, such as a body of a surgical microscope or a head of surgical microscope (including an ocular and a lens) connected to a linkage piece in a surgical microscope system, which can be pivoted or swiveled about at least one rotary shaft and which can maintain its position or posture after being pivoted or swiveled. For example, the body of a surgical microscope can be pivoted about a fifth axis and sixth axis of the surgical microscope system. More specifically, the invention relates to a self-balancing device for maintaining a position of the rotary body of the rotary apparatus during its rotation when changing the center of gravity of the rotary body relative to the rotary shaft.

BACKGROUND

An apparatus, which has a main working component being arranged to protrude from a frame or a base thereof and being able to pivot or swivel about one or more rotary shafts, is known. Here, the main working component is called "rotary body", and thus the apparatus including such a working component is called "rotary apparatus," wherein the rotary body needs to be held in a position after pivoting or swiveling when the center of gravity of the rotary body is changed relative to the rotary shaft to permit an operator to work with this rotary body. Such an apparatus is commonly found in the medical facility field, e.g., in the form of a surgical microscope apparatus or a dental diagnosis instrument. In order to allow a suspended rotary body to rotate easily, stop freely, and maintain any position after being pivoted or swiveled, it is known to provide a self-balancing device configured to withstand a new torque (hereafter referred to as "unbalancing torque") generated by the rotary body relative to the rotary shaft due to the change in the center of gravity after pivoting or swiveling, thereby allowing the rotary body to be held in any desired position.

U.S. Pat. No. 5,492,296 discloses an adjustable stand for an optical viewing apparatus such as a surgical microscope. The adjustable stand includes a tilt shaft and a pivot shaft for the microscope. In order to keep the surgical microscope in balance, this patent proposes an energy store for balancing or counterbalancing the gravity torque (i.e., the unbalancing torque) of the surgical microscope, which is formed by a spiral flat spring mounted in a spring housing. The spring housing is located in the carrier connected to the tilt shaft and is rotatable relative thereto with the rotation of the tilt shaft. In this case, when the tilt shaft is rotated (i.e., when the position of the surgical microscope is changed), the spiral flat spring in the spring housing receives the torque developed by the rotation, thereby keeping the surgical microscope in balance even if the center of gravity of the surgical microscope is changed.

However, the above known technical solution suffers from multiple defects. First of all, the torque output from the spiral flat spring is linear, while the center of gravity of the surgical microscope body generally follows a sine curve or a cosine curve relative to the unbalancing torque caused by displacement of the rotary shaft. As a result, the known balancing system has certain limitations in terms of principle or effect and cannot produce a good balancing effect. Secondly, the spiral flat spring is susceptible to degradation of strength caused by repeated bending over a long period of time because of its inherent fatigue strength, and it may even run the risk of fatigue failure. Finally, in order to ensure strength, the balancing system of spiral flat spring type may need a greater mounting space.

SUMMARY

The invention solves the problems in the above-described prior art and provides a novel balancing device. The balancing device outputs torsional torque by using permanent magnets facing to each other. This is a non-contact torque output technique and does not cause fatigue failure. Moreover, the torsional torque thereby generated is changed according to a sine or cosine curve, which matches well the unbalancing torque of a rotary body that needs to be compensated.

In the invention, the term "rotary body" refers to a working component which is extended/protruded or suspended relative to a frame or base of the apparatus, and which can pivot or swing around at least one rotary shaft and needs to be maintained in position after being pivoted or swiveled. Accordingly, the apparatus that includes the rotary body is called "rotary apparatus."

Specifically, a balancing device for a rotary apparatus is provided, the rotary apparatus has a rotary body which is able to pivot or swivel about at least one rotary shaft. According to an aspect of the invention, the balancing device includes a magnet assembly and a torque adjusting mechanism, wherein the magnet assembly at least includes a combination of two or more magnets, and the torque adjusting mechanism is configured to adjust a torque generated by the combination of the two or more magnets.

The balancing device according to various aspects of the invention has the following advantageous technical features, which can be applied solely or in combination in any possible technical manners:

the torque is a torque for balancing/counteracting a torque generated by the center of gravity of the rotary body relative to the rotary shaft;

the two or more magnets include magnetizers;

the magnet assembly includes a first magnet and a second magnet movable relative to each other;

the torque adjusting mechanism is configured to adjust an electric current or a relative position of the two or more magnets so as to adjust the torque generated by the two or more magnets;

the magnets can be radial ring magnets or Halbach array magnets; Neodymium Iron Boron (NdFeB) magnets, samarium cobalt magnets, aluminum-nickel-cobalt magnets, ferrite magnets; permanent magnets, soft magnets, or electromagnets;

the torque adjusting mechanism includes a magnet phase adjusting mechanism, which is configured to adjust an initial relative phase of the poles of the first magnet and/or the second magnet;

the torque adjusting mechanism includes a torque amplitude adjusting mechanism, the torque amplitude adjusting mechanism is configured to adjust a coupling of the first magnet and/or the second magnet;

the balancing device includes a balancing device housing fixedly connected to a frame of the rotary apparatus;

the first magnet and/or the second magnet is/are connected to the rotary shaft in a non-rotatable manner;

the first magnet and the second magnet are each in an annular shape, wherein the second magnet has an inner diameter larger than an outer diameter of the first magnet, and is arranged substantially coaxial with the first magnet, wherein the first magnet and the second magnet are configured to be rotatable relative to each other;

the first magnet and/or the second magnet is/are formed by a plurality of magnet blocks arranged in Halbach array;

the torque amplitude adjusting mechanism includes a drive which is configured to translate at least one of the first and/or the second magnets relative to each other to permit the coupling of the two magnets to change gradually and/or in a stepped manner;

the coupling is defined as the area of a facing part between the first magnet and the second magnet;

the drive includes a first drive member which carries the first magnet or the second magnet and is arranged to translate along the rotary shaft, and a second drive member which can be operated outside of the balancing device housing to actuate the first drive member to translate;

the first drive member is formed by a sleeve slider mounted on the rotary shaft, the sleeve slider having an internal thread at a side facing the second drive member; the second drive member includes a sleeve portion and/or rod portion which have/has an external thread at a side facing the first drive member for engaging the internal thread;

the second drive member further includes a manipulation member connected to the sleeve portion and/or the rod portion and located outside of the balancing device housing, the manipulation member is used to manipulate the torque amplitude adjusting mechanism;

the manipulation member is configured to have a structure like a steering wheel or a rudder, or is in the form of a hand wheel;

the torque amplitude adjusting mechanism further includes a magnet position indicator which include a follow-up member associated with the first magnet or the second magnet, and a display unit visible from the outside of the balancing device, the follow-up member is configured to change a display state of the display unit as a function of a movement of the first magnet or the second magnet;

the follow-up member includes a push rod and a sleeve cone, an end of the push rod is placed on an outer surface of the sleeve cone that is translatable with the first magnet or the second magnet to permit to reciprocate in a radial direction along with axial translation of the first or second magnet; the display state of the display unit is set to change with the radial reciprocating movement of the push rod;

the magnet phase adjusting mechanism includes a member that can be operated from outside of the balancing device to impart rotation of the first magnet and/or the second magnet;

the magnet phase adjusting mechanism includes a rotating ring arranged on an outer peripheral surface of the balancing device housing;

the magnet phase adjusting mechanism further includes a locking ring, which is arranged side by side with the rotating ring on the outer peripheral surface of the balancing device housing and which has teeth on an end face opposite to the rotating ring configured for engaging with teeth on a corresponding end face of the rotating ring;

the magnet phase adjusting mechanism includes a worm gear configured to rotate with the first magnet or the second magnet, and a worm mounted in the balancing device housing and extending to the outside thereof for rotating the worm to cause the worm gear and the first magnet or the second magnet to rotate;

an end of the worm extending to the outside of the balancing device housing is provided with a hand wheel for manipulation;

the balancing device is arranged on a rotary shaft segment of the rotary shaft, is detachably connected to the rest of the rotary shaft;

the torque adjusting mechanism is driven by an electric motor; and the rotary apparatus is a surgical microscope system, and the rotary body is a body of surgical microscope.

BRIEF DESCRIPTION OF THE DRAWINGS

The invention will now be described with reference to the drawings wherein.

DESCRIPTION OF EXEMPLARY EMBODIMENTS

Figure 1:
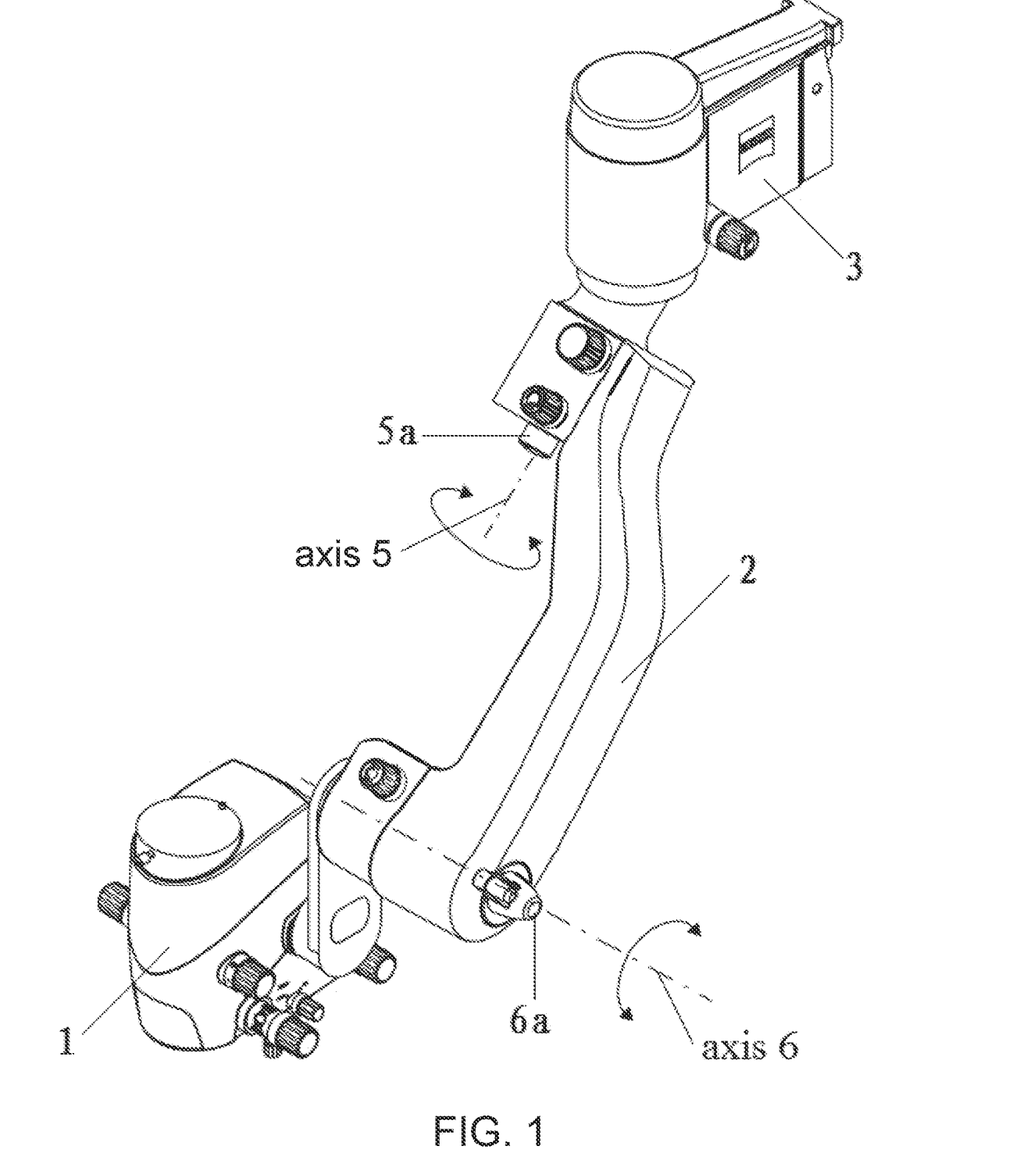
FIG. 1 shows an apparatus to which a balancing device of the invention can be applied according to an exemplary embodiment of the invention.

Referring to FIG. 1, a surgical microscope system is shown as an example of the rotary apparatus. The surgical microscope system includes a body 1 of surgical microscope body which is carried by a linkage piece 2 and which is configured to swivel about axis 5 and pivot about axis 6. A rotary shaft 5a defines said axis 5, and a rotary shaft 6a defines said axis 6. The linkage piece 2 connects the rotary shaft 5a and the rotary shaft 6a. The linkage piece 2 is attached to a stand body of the surgical microscope system by a connecting interface 3.

In use, the body 1 of surgical microscope is aligned with a surgical site of the patient quickly and accurately. For this, the body 1 of surgical microscope is required to swivel from left to right or to pivot back and forth about the rotary shafts 5a and 6a, respectively, as a rotary body, and to maintain its position after it has been pivoted or swiveled over a certain angle. However, such movements will result in a change in the center of gravity of the body 1 of the surgical microscope relative to the position of the rotary shafts, and thus generate a new unbalancing torque relative to the corresponding rotary shaft. This unbalancing torque makes the body 1 of surgical microscope tend to move (pivot or swivel) after being aligned with the surgical site of the patient.

In addition, sometimes it is necessary to attach an assistant scope (co-observer) (not shown) to the body 1 of the surgical microscope to allow an auxiliary, e.g., an assistant of a doctor, to view the process of an operation. Usually, this assistant scope is relatively heavy and attached to extend a relative long distance from the body 1 of the surgical microscope. Consequently, the attachment of the assistant scope also results in a significant change in the center of gravity of the whole rotary body, and thus generates an unbalancing torque. Similarly, the unbalancing torque imparts a tendency of moving continuously to the rotary body including the body 1 of the surgical microscope and the assistant scope.

For counteracting or eliminating the above unbalancing torque so as to prevent the body 1 of the surgical microscope from moving forward and to allow the body 1 of the surgical microscope to rest and stop in an angular position after being pivoted or swiveled, a balancing device is provided for the body 1 of the surgical microscope according to an exemplary embodiment of the invention. In the following, the balancing device arranged on the rotary shaft 6a according to the exemplary embodiment is described. However, it should be understood that the balancing device may also be arranged on the rotary shaft 5a to keep the body 1 of the surgical microscope in balance relative to the rotary shaft 5a. It can be also be conceived to arrange the balancing device on both the rotary shaft 5a and the rotary shaft 6a.

The invention provides a magnetic balancing device including a magnet assembly and a torque adjusting mechanism. The magnet assembly includes at least two magnets movable, e.g. rotatable and translatable, relative to each other. The torque adjusting mechanism may include a mechanism for adjusting the coupling of the two magnets, and a mechanism for adjusting initial relative phases of the two magnets. The two magnets may consist of two spaced permanent magnets or electromagnets and may output a torsional torque which follows a cosine curve or a sine curve in a non-contact manner.

Figure 2:
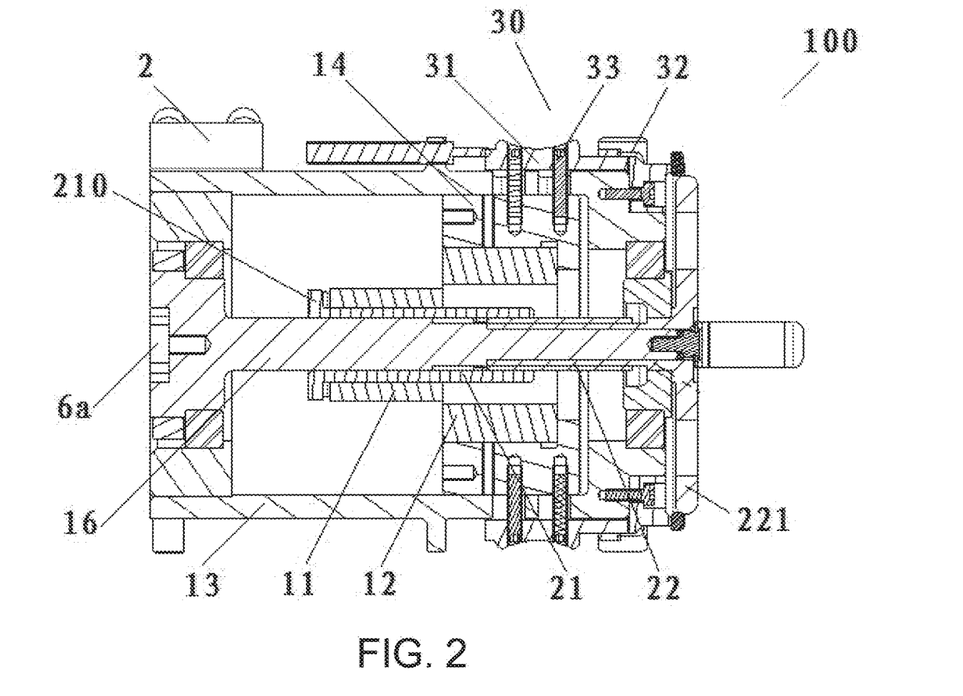
FIG. 2 is a sectional view which shows a balancing device according to an exemplary embodiment of the invention.

Referring to FIG. 2, a sectional view of a balancing device 100 according to a first exemplary embodiment of the invention is shown. The balancing device 100 has a balancing device housing 13 connected to a linkage piece 2 or a stand of the surgical microscope system. Within the balancing device housing 13, a first magnet 11 and a second magnet 12 are provided. The first magnet 11 is arranged on a rotary shaft segment 16 of the rotary shaft 6a in a non-rotatable manner, and the rotary shaft segment 16 may be detachably connected to an end part of the rotary shaft 6a or may be an integral part of the rotary shaft 6a. The second magnet 12 is arranged opposite to the first magnet 11 within the balancing device housing 13, in particular within a magnet shell 14 located in the balancing device housing 13. The second magnet 12 is fixed to the magnet shell 14.

In this way, when an operator, such as a surgeon, pulls, pushes, rotates or swivels the body 1 of the surgical microscope mounted on the rotary shaft 6a to adjust its position or posture, the rotary shaft 6a rotates with the rotation of the body 1 of the surgical microscope, and meanwhile the first magnet 11 rotates with the rotation of the rotary shaft 6a. At this time, the second magnet 12 arranged in the balancing device housing 13 is kept stationary. The relative rotation between the first magnet 11 and the second magnet 12 generates a torsional torque which follows a cosine curve or a sine curve by a magnetic force, such that the unbalancing torque generated by the rotation of the body 1 of the surgical microscope relative to the rotary shaft 6a may be counteracted.

According to a first exemplary embodiment of the invention, as shown in FIG. 2, the first magnet 11 and the second magnet 12 are configured to have an annular shape, wherein an inner diameter of the second magnet 12 is larger than an outer diameter of the first magnet 11. In this way, the first magnet 11 is in the form of an inner magnet mounted around the rotary shaft segment 16, and the second magnet 12 is in the form an outer magnet arranged around the inner magnet.

Figure 3A:
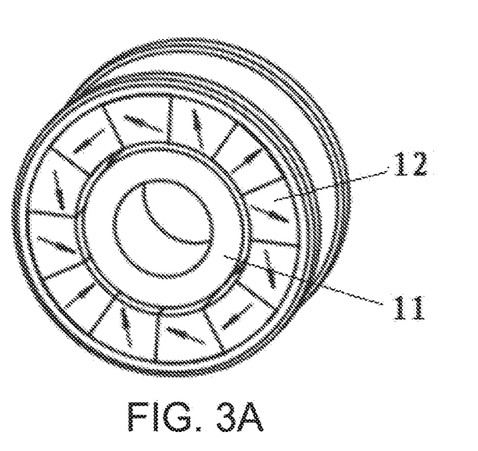
FIGS. 3A and 3B show exemplary embodiments of a first magnet and a second magnet, respectively.
Figure 3B:
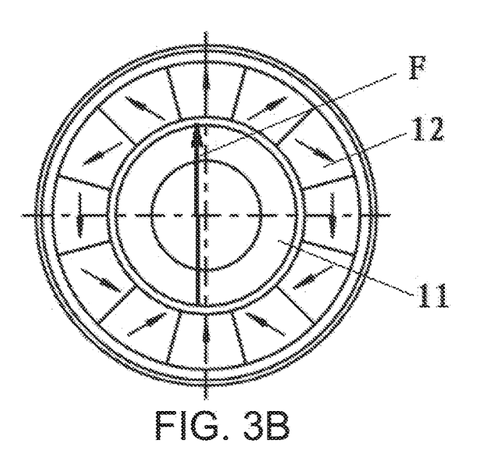

In this case, typically, the outer magnet 12 is formed by a plurality of, typically twelve magnet blocks which are bonded to form a ring and in a Halbach array in terms of magnetizing direction and positions, as shown in FIGS. 3A and 3B. Here, the inner magnet 11 is configured as a magnet ring magnetized in a radial direction as shown by the arrow F in FIG. 3B.

Still referring to FIG. 2, the torque adjusting mechanism of the balancing device 100 according to the exemplary embodiment of the invention includes a torque amplitude adjusting mechanism for adjusting coupling between the first magnet 11 and the second magnet 12. Specifically, the torque amplitude adjusting mechanism adjusts the amplitude of the torsional torque generated during relative rotation of the magnets 11, 12 by adjusting areas ("inductive area") of facing surfaces of the first magnet 11 and the second magnet 12.

Figure 4A:
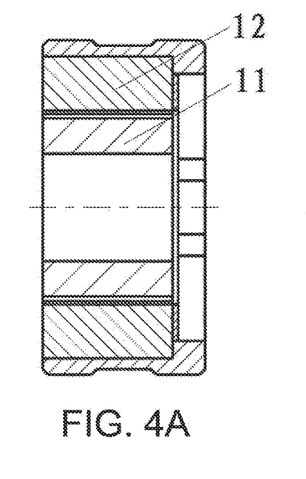
FIGS. 4A to 4C show different coupling states of the first magnet and the second magnet.
Figures 4B, 4C:
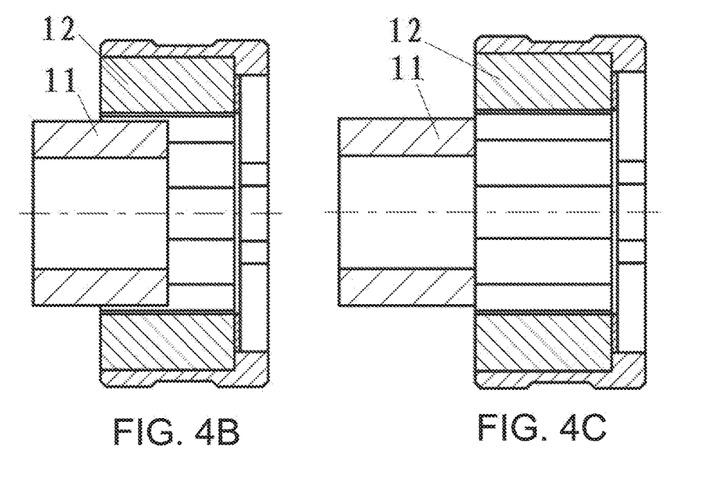
Figure 7:
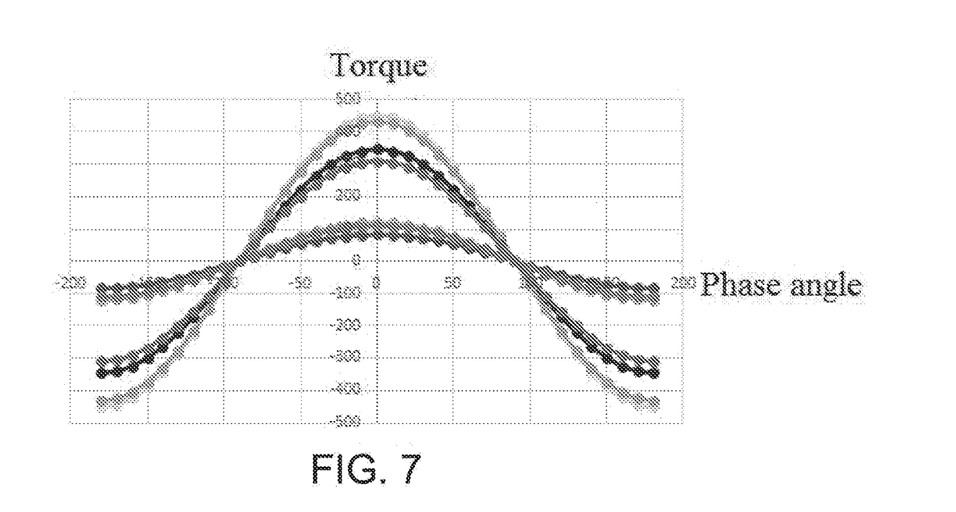
FIG. 7 shows a curve of a torsional torque output by the balancing device according to an exemplary embodiment of the invention.

The torque amplitude adjusting mechanism may be configured in such a manner that the first magnet 11 as the inner magnet and the second magnet 12 as the outer magnet are relatively moved gradually among a fully coupled state (as shown in FIG. 4A), a partly coupled state (as shown in FIG. 4B), and a separated state (as shown in FIG. 4C), so that the amplitude of the torsional torque generated during rotation of the first magnet 11 and the second magnet 12 in 360 degree relative to each other increases or decreases regularly (as shown in FIG. 7).

Specifically, when the first magnet 11 and the second magnet 12 are fully coupled, i.e., when the first magnet 11 is placed entirely inside the second magnet 12, the area of the facing part between the outer surface of the first magnet 11 and the inner surface of the second magnet 12 is maximal, and a maximum amplitude of torsional torque generated by the relative rotation of 360° is created. When the first magnet 11 and the second magnet 12 are partly coupled, i.e., when the first magnet 11 is placed partly inside the second magnet 12, an intermediate amplitude of torsional torque generated during the relative rotation of 360° is created. When the first magnet 11 is separated from the second magnet 12, i.e., when there is no facing part between the outer surface of the first magnet 11 and the inner surface of the second magnet 12, the amplitude of torsional torque generated during the relative rotation of 360° is at a minimum or zero.

Returning to FIG. 2, according to the exemplary embodiment shown in FIG. 2, the torque amplitude adjusting mechanism may include a drive configured to drive the first magnet 11 to slide or translate along the rotary shaft segment 16. The drive may include a first drive member 21, which carries the first magnet 11 to move it therewith, and a second drive member 22, which can be operated outside of the balancing device 100 and is used to actuate the first drive member 21 so as to translate it along the rotary shaft segment 16. The first magnet 11, the first drive member 21, and the rotary shaft segment 16 are configured to be non-rotational relative to one another.

Figure 5:
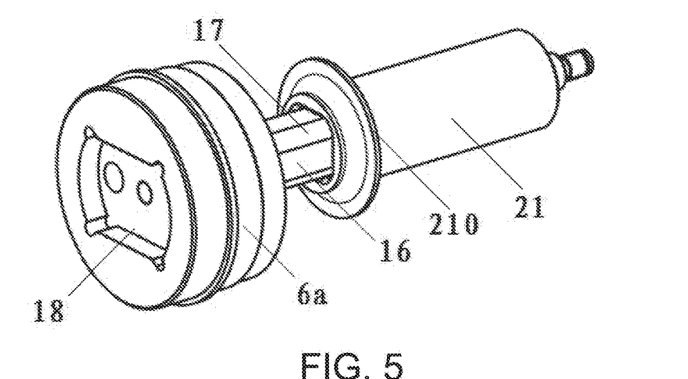
FIG. 5 is a perspective view showing an exemplary embodiment of a drive of a torque amplitude adjusting mechanism.

As can be seen from FIG. 2, the first drive member 21 is typically in the form of a sleeve slider located on a periphery of the rotary shaft segment 16. The annular first magnet 11 is fixed to a circumferential surface of the first drive member 21, for example, by bonding. As best illustrated in FIG. 5, the first drive member 21 is fitted on the rotary shaft segment 16 by a key connection 17. Here, the rotary shaft segment 16 is part of the rotary shaft that is detachably connected to the rest of the rotary shaft 6a by, for example, a non-circular interface 18. Of course, the rotary shaft segment 16 may also be a part integrated with the rotary shaft 6a.

Still referring to FIG. 2 and in combination with FIG. 5, in the exemplary embodiment shown in FIGS. 2 and 5, at an end of the first drive member 21 towards the rotary shaft 6a, a radially projecting flange 210 is provided for fixing or positioning the first magnet 11 on its circumferential surface.

According to the first exemplary embodiment of the invention, the first drive member 21 in the form of a sleeve slider has an internal thread at a side away from the rotary shaft 6a, the internal thread extending over a certain length in an axial direction of the first drive member 21 (i.e., in a left-right direction in FIG. 2). The second drive member 22 may be configured as a sleeve positioned on the periphery of the rotary shaft segment 16 or a rod member coaxial with the rotary shaft segment 16. The second drive member 22 and the rotary shaft segment 16 are in non-contact or smooth contact, such that relative sliding and free rotation can be created therebetween. The second drive member 22 has an outer diameter matching with the inner diameter of the first drive member 21, and an external thread engaged with the internal thread of the first drive member 21.

In this way, when the second drive member 22 is rotated, due to thread screwing of its external thread with the internal thread of the first drive member 21, the first drive member 21 carrying the first magnet 11 will translate or slide along the axial direction on the rotary shaft segment 16, thus changing the area of the facing part between the first magnet 11 and the second magnet 12. In this process, there is no relative rotation among the first magnet 11, the first drive member 21, and the rotary shaft 6a. The rotary shaft 6a and the rotary shaft segment 16 are also configured to not rotate with the rotation of the second drive member 22.

As an alternative exemplary embodiment not shown in the drawings, it is possible that the first drive member 21 and the second drive member 22 are combined to form a single drive member. The single drive member is configured as, e.g., a sleeve mounted on the rotary shaft segment 16 and having an internal thread. The internal thread of the sleeve engages the external thread on the corresponding rotary shaft segment 16 so as to translate the first magnet 11 on the rotary shaft segment 16 by gradually screwing in and out.

Back to FIG. 2 again, typically, the second drive member 22 further includes a manipulation member 221 that can be accessed and operated by an operator. The manipulation member 221 is integrated with the rest of the second drive member 22 or connected therewith in a detachable manner and is rotated by the operator to rotate the second drive member 22 such that the first magnet 11 is driven to axially translate or slide along the rotary shaft segment 16. In the exemplary embodiment shown in FIG. 2, the manipulation member 221 has a structure similar to a steering wheel or a rudder, as well as a handle or grip protruding axially to facilitate the operator's operation. According to an alternative exemplary embodiment, the manipulation member 221 may also be in the form of a hand wheel.

It should be understood that although in the above described first exemplary embodiment, the first magnet 11 is arranged to move in the axial direction of the rotary shaft to change facing areas of the first magnet 11 and the second magnet 12, it is also possible to make the first magnet 11 stationary while the second magnet 12 is movable, or to make both the first and the second magnets 11 and 12 movable, so as to change the range of facing areas between the two magnets, that is to change the coupling state thereof.

Still as shown in FIG. 2, the torque adjusting mechanism of the balancing device 100 according to the exemplary embodiment of the invention further includes a magnet phase adjusting mechanism 30 configured to adjust initial relative phases of the first magnet 11 and the second magnet 12. According to the first exemplary embodiment shown in FIG. 2, the magnet phase adjusting mechanism 30 includes a rotating ring 31 that can be operated outside of the balancing device 100. In particular, the rotating ring 31 may be mounted around an outer peripheral surface of the balancing device housing 13 and connected to the magnet shell 14 by screws 33, for example. Particularly, the screws 33 pass through sliding slots formed in the balancing device housing 13.

In this way, the magnet shell 14 may be driven by rotating the rotating ring 31 outside of the balancing device 100, and thereby causing the second magnet 12 to rotate, which changes the relative phase between the second magnet 12 and the first magnet 11.

Typically, the magnet phase adjusting mechanism 30 further includes a locking ring 32 arranged side by side with the rotating ring 31 on the outer peripheral surface of the balancing device housing 13. In particular, the locking ring 32 is provided with teeth on an axial end face opposing to the rotating ring 31 so as to engage with teeth arranged correspondingly on the rotating ring 31, thereby locking the rotating ring 31 upon completion of the phase adjustment.

The magnet phase adjusting mechanism 30 is not limited to the above exemplary embodiments, and the adjustment of initial phase may be achieved either by rotating the first magnet 11 or by rotating the second magnet 12. For example, it can be conceived to form raised portions (not shown) on the magnet shell 14 which accommodates the second magnet 12, and the raised portions are configured to be exposed or accessed through sliding slots formed in the balancing device housing 13 from the outside of the balancing device 100, such that it is possible to rotate the magnet housing 14 and the second magnet 12 contained therein. For example, teeth (not shown) may be disposed on the flange 210 of the first drive member 21 and may be used to control and adjust the rotation of the first magnet 11, so as to realize the adjustment of relative phase. Here, accordingly, the torque amplitude adjusting mechanism is configured to cause the second magnet 12 to move relative to the first magnet 11.

Figure 6A:
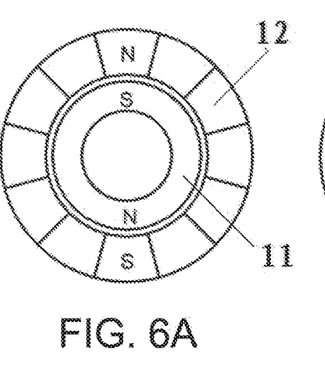
FIGS. 6A to 6C show different initial relative phases of the first magnet and the second magnet.
Figure 6B:
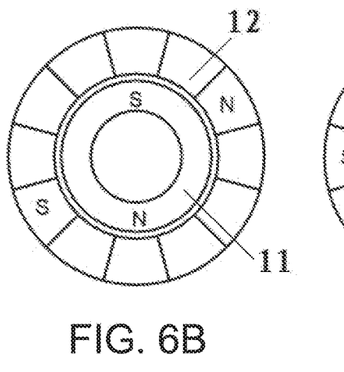
Figure 6C:
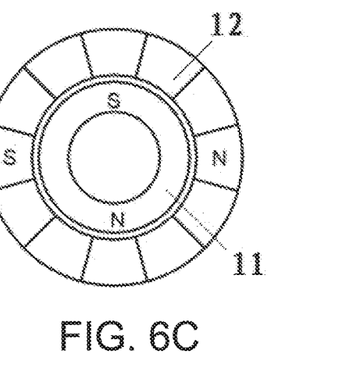

When a surgical microscope apparatus shown in FIG. 1, taken as an example, is provided with the body 1 of the surgical microscope, and it is desired to always keep the body balanced relative to the rotary shaft 6a during its use, the balancing device 100 according to the exemplary embodiment of the invention can be mounted on the rotary shaft 6a, specifically on the rotary shaft segment 16 thereof, with the following initial setting:

The initial relative phase of the first magnet 11 and the second magnet 12 are adjusted by the magnet phase adjusting mechanism 30, depending on the center of gravity of the body 1 of the surgical microscope relative to the rotary shaft 6a. That is, the initial relative angle between a connection line of the N and S poles of the first magnet 11 and a connection line of the N and the S poles of the second magnet 12 is adjusted. Specifically, referring to FIGS. 6A to 6C, if the center of gravity of the body 1 of the surgical microscope is exactly below the rotary shaft 6a (torque output is not required now), the initial relative phase of the first magnet 11 and the second magnet 12 is set to be in a state shown in FIG. 6A. If the center of gravity of the body 1 of the surgical microscope is at the left side of the rotary shaft 6a (with reference to the direction in FIGS. 6A to 6C, a torsional torque is required to rotate the first magnet 11 clockwise), the initial relative phase of the first magnet 11 and the second magnet 12 is set to be in a state similar to that shown in FIG. 6B or 6C, depending on the torsional torque. During this process, the center of gravity relative to the rotary shaft 6a can be determined by visual inspection of the posture of the body 1 of the surgical microscope. After the initial setting, during the use of the surgical microscope, the coupling between the first magnet 11 and the second magnet 12 can be adjusted by the torque amplitude adjusting mechanism according to the weight of the body 1 of the surgical microscope, i.e., the unbalancing torque generated by the body 1 of the surgical microscope relative to the rotary shaft 6a, thereby generating a torsional torque to compensate/counteract the unbalancing torque until the body 1 of the surgical microscope is in a horizontal working posture.

The initial setting may be carried out in another way according to an exemplary embodiment: when the magnets are decoupled, that is, when the facing area of the first magnet 11 and the second magnet 12 is minimal or when the first magnet 11 is farthest from the second magnet 12, the rotary body moves freely, and the center of gravity of the rotary body is just vertically below the rotary shaft 6a after moving, the relative phase of the first magnet 11 and the second magnet 12 is directly adjusted to be zero (i.e., the S pole of the first magnet 11 and the N pole of the second magnet 12 is aligned with each other). Next, the coupling between the first magnet 11 and the second magnet 12 is increased by the torque amplitude adjusting mechanism. Finally, the rotary body is centralized to be ready for use under a certain appropriate coupling, thus, the torque output by the magnet assembly and the unbalancing torque generated by the rotary body are matched.

After the above setting and adjustment, the surgical microscope system is ready for use, and the body 1 of the surgical microscope may be pivoted or swiveled to any position relative to the rotary shaft 6a as needed by the operator during its use. Thanks to the balancing device 100 of the invention, the body 1 of the surgical microscope always maintains its angular position without continuous pivoting or swiveling if it is released by the operator after being rotated a certain angle about the rotary shaft 6a. This is due to the fact that the balancing device 100 outputs a torsional torque following a cosine (or sine) curve (as shown in FIG. 7), which is optimally matched with the unbalancing torque during the movement of the center of gravity of the body 1 of the surgical microscope.

Another exemplary embodiment of the invention is illustrated below with reference to FIGS. 8 to 11, which is particularly suitable for a rotary apparatus with a rotary body having two distinct weights. Still, the surgical microscope system is taken as an example. For the surgical microscope system including the assistant scope, the rotary body thereof may have two significantly different weights and centers of gravity: one involves only the weight and the center of gravity of the surgical microscope body, and the other involves the total weight and the center of gravity of the surgical microscope body attached with the assistant scope, thereby generating unbalancing torques of two significantly different amplitudes.

The main difference between the balancing device illustrated in the exemplary embodiment shown in FIGS. 8 to 11 and the balancing device illustrated in the exemplary embodiment shown in FIG. 2 is the torque amplitude adjusting mechanism. Specifically, the torque amplitude adjusting mechanism in the exemplary embodiment shown FIGS. 8 to 11 is configured in such a manner that the areas of the opposite faces of the first magnet 11 and the second magnet 12 only vary according to two coupling states. In other words, although the areas of the opposite faces of the first magnet 11 and the second magnet 12 are changed by driving to couple gradually, a display unit 236 is disposed outside of the balancing device housing 13 to clearly show the two degrees of coupling to the operator.

Figure 8:
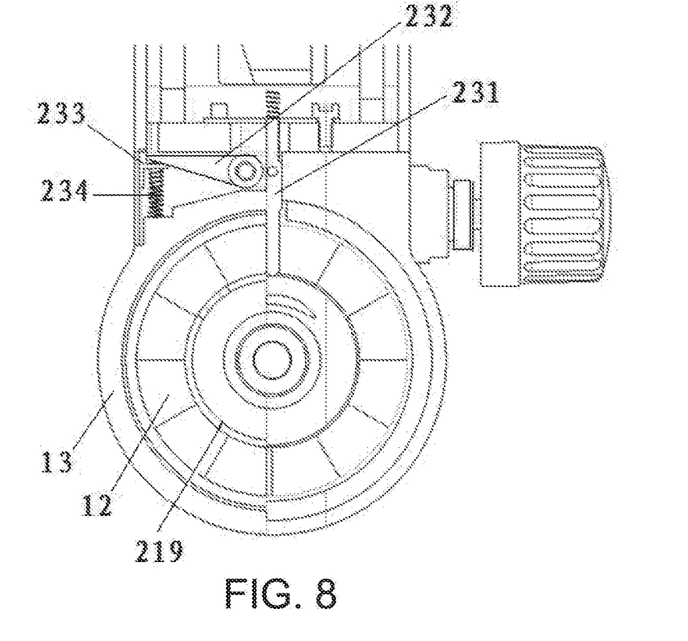
FIG. 8 shows an end view of the balancing device according to another exemplary embodiment of the invention.

Referring to FIG. 8, in this exemplary embodiment, besides the first drive member and the second drive member being similar to the drive members shown in the exemplary embodiment of FIG. 2, the torque amplitude adjusting mechanism further includes magnet position indicators 231-234, which include a display unit 236 (see FIG. 9) that is visible from the outside of the balancing device, and a follow-up member for changing the display state of the display unit 236.

Figure 9:
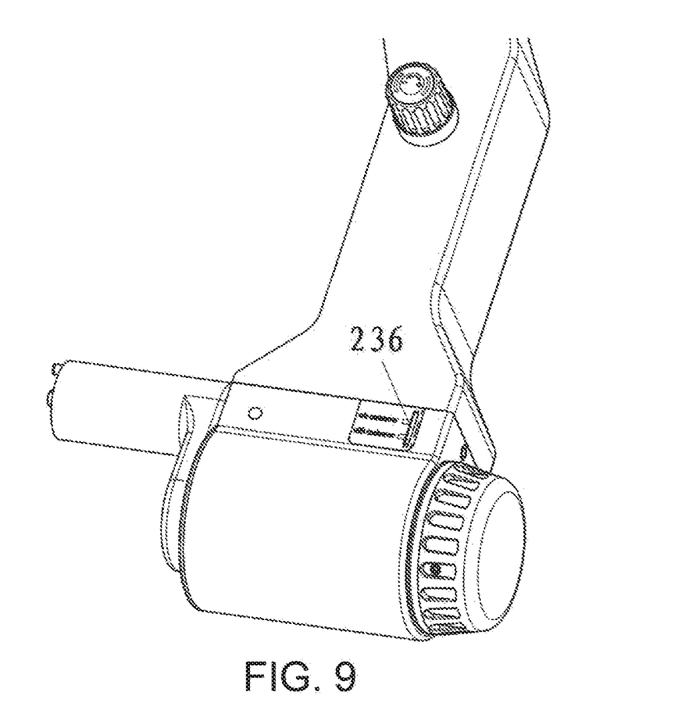
FIG. 9 is an external perspective view of the balancing device shown in FIG. 8.

As shown in FIG. 9, the display unit 236 may include two display marks for indicating a current coupling state of the first magnet and the second magnet, respectively, such that the operator can select settings that match current condition of the apparatus (i.e., whether an assistant scope is mounted). Typically, the display unit 236 may include marks of "with co-observer" and 'without co-observer'."

The follow-up member may be configured to move with the movement of the first magnet 11 so as to indicate a display mark of the display unit 236.

Returning to FIGS. 8 and 11, typically, the follow-up member may include a push rod 231, a lever 232, and a sliding rod 233. An end of the push rod 231 is placed on a conical outer surface of a sleeve cone 219 that is translatable with the first magnet 11. The sleeve cone 219 may be sleeved onto an outer side of the first drive member 21 to translate with the first magnet 11, such that the push rod 231 may reciprocate in a radial direction (lifting or lowering) with the axial translation of the first magnet 11. The lever 232 is connected, e.g., hinged, to the push rod 231, so as to swivel with the reciprocating movement of the push rod 231. In particular, the lever 232 can apply pressure to the sliding rod 233 by an oscillating movement so as to reciprocate the slider rod 233. The sliding rod 233 may be inserted into a slot in the balancing device housing 13, and may be mounted thereto by, e.g., a spring 234. The sliding rod 233 extends from the slot in the balancing device housing 13 and is aligned with one of the display marks on the display unit 236.

Figure 10:
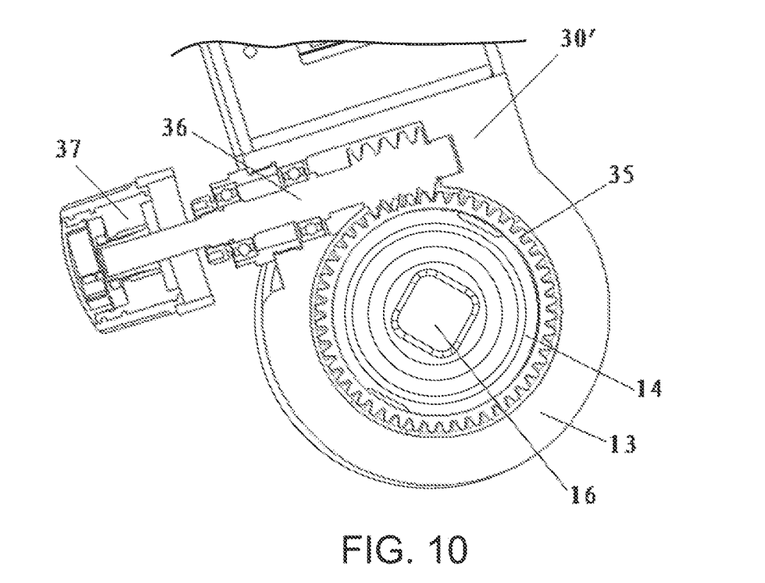
FIG. 10 is a first sectional view of the balancing device shown in FIG. 8.
Figure 11:
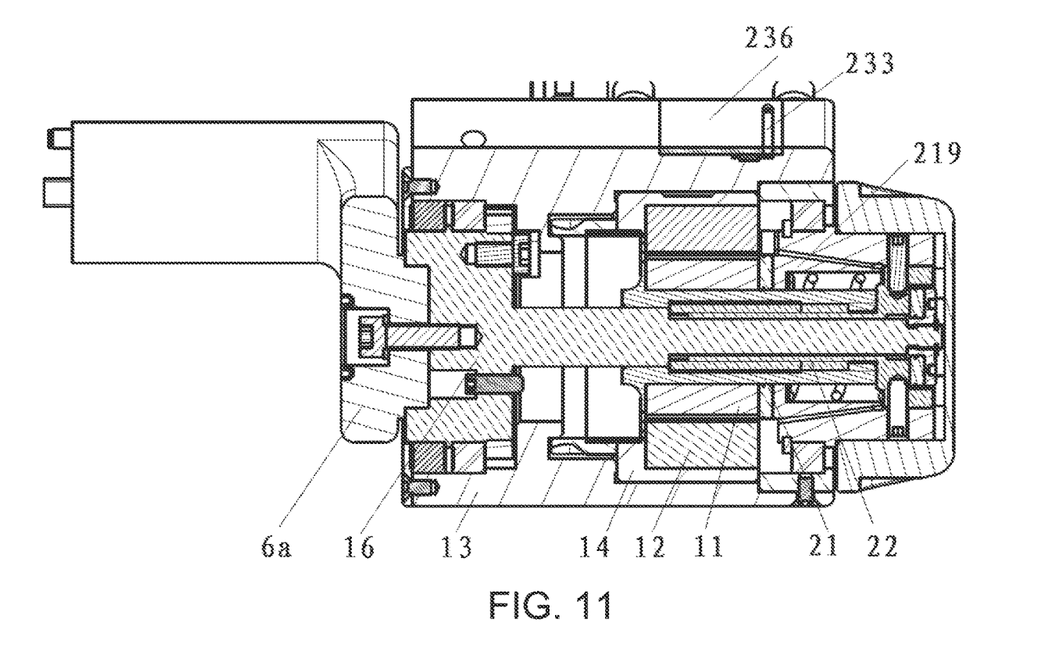
FIG. 11 is a second sectional view of the balancing device shown in FIG. 8

Now referring to FIGS. 10 and 11, an exemplary embodiment of the magnet phase adjusting mechanism 30' is shown. It includes a worm gear 35 which is fixed to the outer peripheral surface of the magnet shell 14 and which is provided with peripheral teeth, and a worm 36 which includes a toothed portion designed to engage with the teeth of the worm gear 35 and a rod portion extending outside of the balancing device. The rod portion is mounted on the balancing device housing 13 by a bearing and is provided with a manipulation member in the form of a hand wheel 37 at an end. In this way, the assembly of the worm gear and the worm can be driven by turning the hand wheel 37, thus causing the magnet shell 14 and the second magnet 12 to rotate, thereby adjusting the initial relative phase of the first magnet 11 and the second magnet 12.

The balancing device of this exemplary embodiment can be used in the following manner. If the surgical microscope apparatus is only equipped with the body 1 of the surgical microscope, the operator may place the first magnet and the second magnet in the coupling state of "without co-observer" by the torque amplitude adjusting mechanism and with reference to the display marks displayed by the display unit 236, and adjust the initial phase of the first magnet and the second magnet by the magnet phase adjusting mechanism 30', so as to achieve the balance of the rotary body which only includes the body 1 of the surgical microscope. If the assistant scope is attached to the body 1 of the surgical microscope, the operator may place the first magnet and the second magnet in the coupling state of "with co-observer" by the torque amplitude adjusting mechanism, and adjust the initial phase of the first magnet and the second magnet by the magnet phase adjusting mechanism 30', so as to achieve the balance of the rotary body including the body of surgical microscope and the assistant scope. Of course, the exemplary embodiment may be modified to apply for a rotary apparatus having more than two significant different weights, as long as the corresponding display marks of the display unit 236 are modified accordingly. For example, when an external camera or any other structure is attached to the body of surgical microscope, an additional display mark can be added to the display unit 236.

According to another exemplary embodiment which is not shown, operation(s) of the torque amplitude adjusting mechanism and/or the magnet phase adjusting mechanism may be realized by a drive of an electric motor. The adjustment may be automatic torsional torque detection and automatic torque generation adjustments by sensors and electrical means.

Although the exemplary embodiments illustrated hereinabove include a surgical microscope system, it should be understood that the application field of the invention is not limited thereto. Instead, the present invention may be applied to any rotary apparatus with a rotary body, for example, processing or operating equipment in the industrial field, tower crane equipment in the construction field, etc. The first and second magnets used in the exemplary embodiments of the invention may be of various types of magnets, such as radial ring magnets or Halbach array magnets, for example, NdFeB magnets, samarium cobalt magnets, aluminum-nickel-cobalt magnets or ferrite magnets, such as permanent magnets or soft magnets or electromagnets.

Finally, it is understood that the foregoing description is that of the exemplary embodiments of the invention and that various changes and modifications may be made thereto without departing from the spirit and scope of the invention as defined in the appended claims.

What is claimed is:

1. A balancing device arranged in a rotary apparatus having a rotary body configured to at least one of pivot and swivel about at least one rotary shaft, the balancing device comprising:
   a balancing device housing having at least one opening;
   a magnet assembly including a first magnet and a second magnet arranged in the balancing device housing to be rotatable and translatable relative to one another; and
   a torque adjusting mechanism configured to adjust a torque generated by the first and second magnets and including a magnet phase adjusting mechanism,
   wherein the torque is a first torsional torque,
   wherein the first torsional torque is adjusted by the torque adjusting mechanism such that the first torsional torque compensates a second unbalancing torque generated when a center of gravity of the rotary body relative to the at least one rotary shaft changes,
   wherein the magnet phase adjusting mechanism includes a member configured to be operated from an outside of the balancing device to impart rotation of at least one of the first magnet and the second magnet,
   wherein at least one of the first magnet and a second magnet is arranged in a magnet shell,
   wherein the member is connected to the magnet shell by at least one connecting element extending through the at least one opening in the balancing device housing, and
   wherein the member, the magnet shell, and the at least one connecting element are movable as a unit relative to the balancing device housing.

2. The balancing device according to claim 1, wherein the first and second magnets include magnetizers.

3. The balancing device according to claim 1, wherein the torque adjusting mechanism is configured to adjust at least one of an electric current and relative positions of the first and second magnets to permit the torque generated by the first and second magnets to be adjusted.

4. The balancing device according to claim 1, wherein the first and second magnets are at least one of radial ring magnets, Halbach array magnets, Neodymium Iron Boron (NdFeB) magnets, samarium cobalt magnets, aluminum-nickel-cobalt magnets, ferrite magnets, permanent magnets, soft magnets, and electromagnets.

5. The balancing device according to claim 1, wherein the magnet phase adjusting mechanism is configured to adjust an initial relative phase between poles of the first magnet and the second magnet.

6. The balancing device according to claim 5, wherein the member is a rotating ring.

7. The balancing device according to claim 6, wherein the rotating ring is arranged on an outer peripheral surface of the balancing device housing.

8. The balancing device according to claim 7, wherein:
   the magnet phase adjusting mechanism further includes a locking ring,
   the locking ring is arranged side by side with the rotating ring on an outer peripheral surface of the balancing device housing, and
   the locking ring is configured to engage with the rotating ring.

9. The balancing device according to claim 1, wherein the torque adjusting mechanism includes a torque amplitude adjusting mechanism configured to adjust a coupling of the first magnet and the second magnet.

10. The balancing device according to claim 9, wherein the torque amplitude adjusting mechanism includes a drive configured to move at least one of the first magnet and the second magnet relative to each other to permit the coupling of the first magnet and the second magnet to be changed at least one of gradually and in a stepped manner.

11. The balancing device according to claim 10, wherein the coupling is defined as an area between the first magnet and the second magnet in which the first and the second magnets face each other.

12. The balancing device according to claim 10, wherein the drive includes a first drive member and a second drive member, the first drive member carries at least one of the first magnet or the second magnet, the first drive is configured to move along the at least one rotary shaft, and the second drive member is operated outside of the balancing device housing to actuate the first drive member.

13. The balancing device according to claim 12, wherein:

the first drive member is a sleeve slider mounted on the at least one rotary shaft, the sleeve slider has an internal thread at a side facing the second drive member, the second drive member includes at least one of a sleeve portion and rod portion, and the at least one of the sleeve portion and the rod portion has an external thread at a side facing the first drive member configured to engage the internal thread.

14. The balancing device according to claim 13, wherein:

the second drive member further includes a manipulation member connected to the at least one of the sleeve portion and the rod portion, the second drive member is located outside of the balancing device housing, and the manipulation member is configured to manipulate the torque amplitude adjusting mechanism.

15. The balancing device according to claim 14, wherein the manipulation member is configured to at least one of (a) have a structure like a steering wheel, (b) have a structure like a rudder, and (c) be in a form of a hand wheel.

16. The balancing device according to claim 1, further comprising a balancing device housing and a frame of the rotary apparatus, the balancing device housing being fixedly connected to the frame of the rotary apparatus.

17. The balancing device according to claim 1, wherein at least one of the first magnet and the second magnet is fixedly mounted on the at least one rotary shaft.

18. The balancing device according to claim 1, wherein:

each of the first magnet and the second magnet has an annular shape, an inner diameter, and an outer diameter, the inner diameter of the second magnet is larger than the outer diameter of the first magnet, and the second magnet is arranged substantially coaxial with the first magnet.

19. The balancing device according to claim 1, wherein at least one of the first magnet and the second magnet is formed by a plurality of magnet blocks arranged in a Halbach array.

20. The balancing device according to claim 1, wherein:

the rotary shaft includes a rotary shaft segment, the first magnet is arranged on the rotary shaft segment, and the rotary shaft segment is detachably connected to an end of the rotary shaft.

21. The balancing device according to claim 1, wherein the rotary apparatus is a surgical microscope system, and wherein the rotary body is a body of a surgical microscope.

22. The balancing device according to claim 1, wherein:

the member is a rotating ring, the connecting element is a screw, and the rotating ring is fastened to the magnet shell by the screw.

* * * * *